United States Patent
Saber et al.

(10) Patent No.: US 12,246,142 B2
(45) Date of Patent: Mar. 11, 2025

(54) LOAD SENSING SYSTEM FOR PERCUTANEOUS DEVICE WITH A CURVED PATH

(71) Applicant: Corindus, Inc., Waltham, MA (US)

(72) Inventors: Omid Saber, Waltham, MA (US); Saeed Sokhanvar, Belmont, MA (US)

(73) Assignee: Siemens Healthineers Endovascular Robotics, Inc., Newton, MA (US)

( * ) Notice: Subject to any disclaimer, the term of this patent is extended or adjusted under 35 U.S.C. 154(b) by 918 days.

(21) Appl. No.: 16/850,531

(22) Filed: Apr. 16, 2020

(65) Prior Publication Data

US 2020/0338308 A1   Oct. 29, 2020

Related U.S. Application Data (60) Provisional application No. 62/839,921, filed on Apr. 29, 2019.

(51) Int. Cl.
| | | |
|---|---|---|
| *A61M 25/01* | (2006.01) | |
| *A61B 34/00* | (2016.01) | |
| *A61B 90/00* | (2016.01) | |
| *G01L 5/16* | (2020.01) | |

(52) U.S. Cl.
CPC ........... *A61M 25/0113* (2013.01); *G01L 5/16* (2013.01); *A61B 34/76* (2016.02); *A61B 2090/064* (2016.02); *A61B 2090/066* (2016.02); *A61M 25/0116* (2013.01); *A61M 2205/332* (2013.01)

(58) Field of Classification Search
CPC ................. G01L 5/16; A61B 2090/064; A61B 2090/066; A61M 25/01; A61M 25/0102; A61M 25/0105; A61M 2025/0166
See application file for complete search history.

(56) References Cited

U.S. PATENT DOCUMENTS

| | | |
|---|---|---|
| 7,887,549 B2 | 2/2011 | Wenderow et al. |
| 7,984,659 B2 | 7/2011 | Fujimoto et al. |
| 8,631,713 B2 | 1/2014 | Fukimoto |
| 2002/0128633 A1 | 9/2002 | Brock et al. |
| 2005/0218386 A1 | 10/2005 | Giroux |
| 2007/0060879 A1 | 3/2007 | Weitzner et al. |
| 2009/0229381 A1 | 9/2009 | Fujimoto et al. |
| 2010/0130987 A1 | 5/2010 | Wenderow et al. |
| 2010/0292566 A1* | 11/2010 | Nagano ................. A61B 17/12 600/587 |
| 2016/0338783 A1* | 11/2016 | Romo .................... A61B 90/06 |
| 2017/0035991 A1* | 2/2017 | Rankin .................. A61B 18/18 |

FOREIGN PATENT DOCUMENTS

| | | |
|---|---|---|
| WO | 2005000105 A2 | 1/2005 |

\* cited by examiner

*Primary Examiner* — Tammie K Marlen
*Assistant Examiner* — Megan T Fedorky (57) ABSTRACT

An apparatus includes a base and a support including a non-straight channel extending therethrough. An elongated medical device extends through the channel and imparts a first load to a channel wall causing a reaction load on the support. A sensor is configured to measure a reaction load applied to the support.

20 Claims, 9 Drawing Sheets

LOAD SENSING SYSTEM FOR PERCUTANEOUS DEVICE WITH A CURVED PATH

CROSS-REFERENCE TO RELATED PATENT APPLICATIONS

This application claims the benefit of U.S. Provisional Application No. 62/839,921 filed on Apr. 29, 2019 entitled Load Sensing System for Percutaneous Devices with a Curved Path incorporated herein by reference in its entirety.

BACKGROUND

Catheters (and other elongated medical devices) may be used for many minimally-invasive medical procedures for the diagnosis and treatment of diseases of various vascular systems, including neurovascular interventional (NVI) also known as neurointerventional surgery, percutaneous coronary intervention (PCI) and peripheral vascular intervention (PVI). These procedures typically involve navigating a guidewire through the vasculature, and via the guidewire advancing a working catheter to deliver therapy. The catheterization procedure starts by gaining access into the appropriate vessel, such as an artery or vein, with a sheath or guide catheter using standard percutaneous techniques. The sheath or guide catheter is then advanced over a diagnostic guidewire to the primary location such as an internal carotid artery for NVI, a coronary ostium for PCI or a superficial femoral artery for PVI. A guidewire suitable for the vasculature is then navigated through the sheath or guide catheter to a target location in the vasculature. In certain situations, such as in tortuous anatomy, a support catheter or microcatheter is inserted over the guidewire to assist in navigating the guidewire. The physician or operator may use an imaging system (e.g., fluoroscope) to obtain a cine with a contrast injection and select a fixed frame for use as a roadmap to navigate the guidewire or catheter to the target location, for example a lesion. Contrast-enhanced images are also obtained while the physician delivers the guidewire or catheter device so that the physician can verify that the device is moving along the correct path to the target location. While observing the anatomy using fluoroscopy, the physician manipulates the proximal end of the guidewire or catheter to direct the distal tip into the appropriate vessels toward the lesion and avoid advancing into side branches.

Robotic catheter procedure systems have been developed that may be used to aid a physician in performing catheterization procedures such as, for example, NVI, PCI and PVI. Examples of neurovascular intervention (NVI) catheter procedures include coil embolization of aneurysms, liquid embolization of arteriovenous malformations and mechanical thrombectomy of large vessel occlusions in the setting of acute ischemic stroke. In NVI, the physician uses a robotic system to gain lesion access by manipulating a neurovascular guidewire and microcatheter to deliver the therapy to restore normal blood flow. The access is enabled by the sheath or guide catheter but may also require an intermediate catheter for more distal territory or to provide adequate support for the microcatheter and guidewire. The distal tip of a guidewire is navigated into, or past, the lesion depending on the type of lesion and treatment. For treating aneurysms, the microcatheter is advanced into the lesion and the guidewire is removed and several coils are deployed into the aneurysm through the microcatheter and used to embolize the aneurysm. For treating arteriovenous malformations, a liquid embolic is injected into the malformation via a microcatheter. Mechanical thrombectomy to treat vessel occlusions can be achieved either through aspiration or use of a stent retriever. Aspiration is either done directly through the microcatheter, or with a larger bore aspiration catheter. Once the aspiration catheter is at the lesion, negative pressure is applied to remove the clot through the catheter. Alternatively, the clot can be removed by deploying a stent retriever through the microcatheter. Once the clot has integrated into the stent retriever, the clot is retrieved by retracting the stent retriever and microcatheter into the guide catheter.

In PCI, the physician uses a robotic system to gain lesion access by manipulating a coronary guidewire to deliver the therapy and restore normal blood flow. The access is enabled by seating a guide catheter in the coronary ostium. The distal tip of the guidewire is navigated past the lesion and, for complex anatomies, a microcatheter may be used to provide adequate support for the guidewire. The blood flow is restored by delivering and deploying a stent or balloon at the lesion. The lesion may need preparation prior to stenting, by either delivering a balloon for pre-dilation of the lesion, or by performing atherectomy using, for example, a laser or rotational atherectomy catheter and a balloon over the guidewire. Diagnostic imaging and physiological measurements may be performed to determine appropriate therapy by using imaging catheters or FFR measurements.

In PVI, the physician uses a robotic system to deliver the therapy and restore blood flow with techniques similar to NVI and PVI. The distal tip of the guidewire is navigated past the lesion and a microcatheter may be used to provide adequate support for the guidewire for complex anatomies. The blood flow is restored by delivering and deploying a stent or balloon to the lesion. As with PCI, lesion preparation and diagnostic imaging may be used as well.

SUMMARY

An apparatus includes a base and a support including a non-straight channel extending through it. An elongated medical device (EMD) extends through the channel and imparts a first load to a channel wall causing a reaction load on the support. A sensor is configured to measure a reaction load applied to the support. The apparatus in one embodiment includes a processor to determine the first load based on the reaction load. The first load applied to the EMD in one embodiment is determined independent of the magnitude of the bending, deflection, and/or buckling of the EMD.

In one embodiment the channel is non-straight and has sufficiently low friction that the error caused by the friction force in determining the force acting on the EMD is below the acceptable error. In one embodiment the channel is non-straight and there is finite friction, with the load magnitude acting on the EMD at the entry of the channel higher than the magnitude acting on the EMD at the exit of the channel, with the entry of the channel being closer to the drive mechanism driving the EMD than the exit of the channel. In the apparatus of this embodiment the finite friction between the EMD and the channel is characterized and is corrected for in determining the load magnitude acting on the EMD at the exit and entry of the channel. In one embodiment the channel is non-straight and the first load applied to the EMD is determined independent of friction between the EMD and the channel.

In one embodiment the apparatus further includes a drive mechanism moving the EMD in at least one direction, with the first load applied to the EMD determined independent of the drive mechanism used to manipulate the EMD. In one embodiment the sensor is grounded relative to the base. In one embodiment the first load is a force in compression or tension acting along a longitudinal axis of the EMD. In one embodiment the first load is a torque acting on the EMD in a clockwise or counterclockwise direction about the longitudinal axis of the EMD.

In one embodiment the support is fixed relative to the base near the entry and exit of the channel, where the entry and exit axes are non-colinear. In one embodiment the support is rigid between the entry and exit of the channel. In another embodiment the support is flexible between the entry and exit of the channel. In one embodiment the channel includes an arcuate portion intermediate the entry and exit. In one embodiment an exit longitudinal axis of the channel extends in a direction distally from the exit and spaced from an entry longitudinal axis of the EMD that extends in a direction proximally from the entry. In one embodiment the exit and entry longitudinal axes are parallel. In one embodiment the channel includes more than one radius of curvature. In one embodiment the channel includes at least one inflection point.

In one embodiment of the apparatus a portion of the EMD enters, moves through, and exits the channel and the load measured is the load acting on the EMD near the channel exit. In one embodiment the apparatus includes a linear slide allowing the support to move relative to the base in a single degree of freedom perpendicular to an entry axis. In one embodiment the sensor is positioned within a reusable base and the support is positioned within a cassette removably coupled to the base. In one embodiment of the apparatus the cassette and the reusable base are separated by one or more sterile barriers. In one embodiment of the apparatus the sensor is removably coupled to the support with a coupler. In one embodiment the support includes a slit to permit radial loading of the EMD into the channel.

In one embodiment of the apparatus a multi-axis sensor detects a load along more than one axis. In one embodiment the multi-axis sensor determines the actual axial force and torque applied to the EMD independent of friction between the EMD and the channel by measuring a component of a reaction force and a torque imparted to the channel by the EMD.

In one embodiment the first load is an axial force and the sensor is a torque sensor measuring a reaction torque on the support. In one such embodiment an axis at the entry of the channel intersects with an axis of the torque sensor so that the reaction torque measured by the sensor is independent of a friction force between the EMD and the channel and is only a function of an actual force acting on the EMD.

In one embodiment the first load is a force and a second load is a torque and a multi-axis sensor measures the reaction force and reaction torque on the support to determine the force and the torque applied to the EMD. In one embodiment the first load is a torque and a force sensor measures the reaction force on the support to determine the torque applied to the EMD. In one such embodiment the support is a tube.

A method of measuring a load on an EMD includes a base and a support with a non-straight channel through it. In moving the EMD through the channel, a sensor measures the reaction load applied to the support from the EMD, where the reaction load is related to the load acting on the EMD. The load-sensing system is used for both a robotic procedure and a manual interventional procedure.

In one embodiment an apparatus includes a base and a support with a non-straight channel through it; extending an EMD through the channel, a sensor measures the reaction load on the support from the load acting on the EMD, where the reaction force is independent of the magnitude of bending, deflection and/or buckling of the EMD. In one embodiment the sensor determines the real-time load acting on the EMD during an operation.

In one embodiment, an apparatus comprising a device for proximal load-sensing on any arbitrary commercial sensorless EMD independent of the load applied to the EMD by an EMD drive mechanism, where the load acting on the EMD is determined while the drive mechanism provides continuous motion of the EMD without requiring resets.

In one embodiment an apparatus includes a device for proximal load-sensing on any arbitrary commercial sensorless EMD independent of forces applied to the EMD by an EMD drive mechanism. The load acting on the EMD is determined while the drive mechanism provides continuous motion of the EMD without requiring resets.

DEFINITIONS & TERMINOLOGY

EMD: An elongated medical device (EMD) includes (but is not limited to) catheters (guide catheters, microcatheters, balloon/stent catheters), wire-based devices (guidewires, embolization coils, stent retrievers, etc.), and devices that have a combination.

Load: The term load is used to refer to forces, torques, or combination of forces and torques. The load may include a single component of force (a force along a single axis) or multiple components of forces (multi-axial forces) and/or a single component of torque (a torque around a single axis) or multiple components of torque (multi-axial torque).

Force: The term force is used here to mean an agent which causes or tends to cause motion of a physical body. While acting on a body a force may change the motion of a body, retard the motion of a body, balance the forces already acting on a body, and give rise to the internal stresses in a body. Characteristics of a force include the magnitude of the force, the line of action of the force (the axis along which the force acts), the direction of the force (corresponding to compressive or tensile force), and the point at which the force is acting.

Torque: The term torque is used here to mean an agent which causes or tends to cause rotational motion of a physical body. While acting on a body a torque may change the rotational motion of a body, retard the rotational motion of a body, balance the torques already acting on a body, and give rise to the internal stresses in a body. Characteristics of a torque include the magnitude of the torque, the line of action of the torque, the direction of the torque (clockwise or counterclockwise about the line of action), and the point at which the torque is acting. The term torque is also referred to as moment, moment of force, rotational force, twisting force, and "turning effect". Torque is the rotational equivalent of force. The magnitude of the torque can also be determined as the product of the magnitude of the force and the perpendicular distance of the line of action of force from the axis of rotation.

Base: The term base is used here to refer to an inertial frame of reference. In this frame of reference, a body with zero net force acting upon it does not accelerate; that is, such a body is at rest or moving at a constant velocity. In an inertial reference frame Newton's laws of motion are valid. As used here, the surface of the Earth is taken as an inertial frame of reference. The term base is also known as ground and is denoted in the figures by short slanted parallel lines.

Distal and Proximal: When applied to an EMD the terms distal and proximal are used in relationship with the operator/physician as the reference point. The side that is closer to an operator (stays outside the patient's body) is known as proximal end and the side that is farther from the operator (normally enters the body) is called distal end. The distal end of an EMD such as a guidewire is the distal free end of the guidewire (wire tip) that is intended to be inserted first into the patient. The proximal free end of the guidewire is the end of the guidewire opposite of the distal free end that is intended to remain outside of a patient during insertion of the guidewire. The most distal portion of the robotic drive is the portion of the robotic drive that is intended to be closest to the insertion point of the EMD into a patient that is controlled by the robotic system. The term proximal is the direction that is opposite to distal.

Longitudinal Axis: The term longitudinal axis of a member is in the general direction of orientation going from a proximal portion of the member to a distal portion of the member. By way of example, the longitudinal axis of a guidewire is the general direction of orientation from a proximal portion of the guidewire toward a distal portion of the guidewire even though the guidewire may be non-linear in the relevant portion. At each point along a member, the longitudinal axis corresponds to the direction of the normal vector of the cross-section area of the member at that point.

Axial Movement: Axial movement of a member is translation in the direction along the longitudinal axis of the member. When a distal end of an EMD is being axially translated in a distal direction along its longitudinal axis into or further into the patient's vasculature, the EMD is being advanced. Alternatively, when an EMD is being withdrawn from a patient the EMD is being axially translated in a proximal direction along its longitudinal axis.

Rotational Movement: Rotational movement of a member is rotation in a direction about its longitudinal axis. By way of example, an EMD is rotated clockwise or counterclockwise about its longitudinal axis in response to an applied torque.

Insert/Withdraw: The term insert refers to the direction in which the EMD is being moved further into a vasculature of a patient, and the term withdraw refers to the action and direction in which the EMD is being moved oppositely of insert, such that the EMD is being moved in a direction such that less and less of the EMD is within the vasculature of a patient.

Sensor: The term sensor as used herein is a transducer that converts compressive and/or tensile force components and/or clockwise and/or counterclockwise torque components into a measurable electrical output (voltage or current). Example transducers include strain-gage-based load cells or load cells that operate by hydraulic, pneumatic, piezoelectric, capacitive, or other means. In one embodiment sensors have fine wires that connect to circuits that either directly or wirelessly transfer information to a processor for signal conditioning and/or computation and processing for display and/or use by a control system for drive system control. In one embodiment the processor is part of the control computing system.

DETAILED DESCRIPTION OF THE EXAMPLE EMBODIMENTS

Figure 1A:
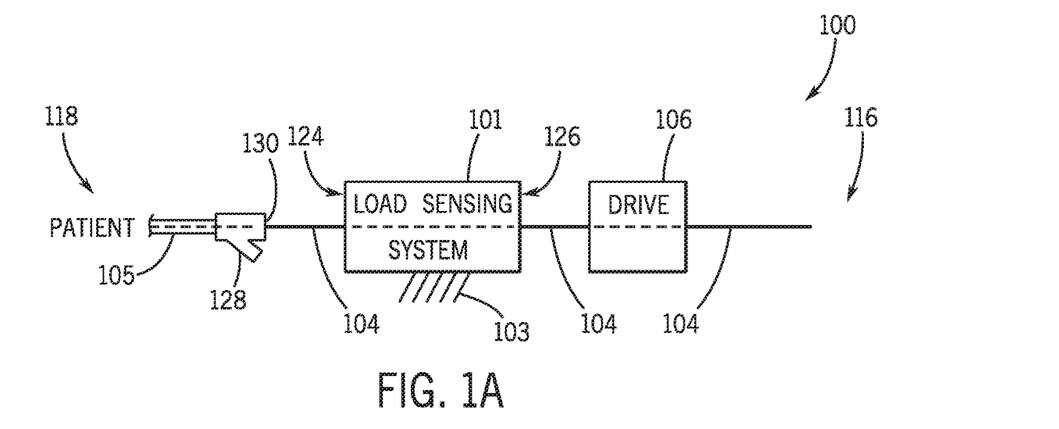
FIG. 1A is a system block diagram of showing a drive and load sensing system for an elongated medical device system (EMD).

Referring to FIG. 1A an elongated medical device (EMD) drive system 100 includes a load sensing system 101 detecting at least one load acting upon an elongated medical device 104 being driven relative to base 103 by a drive 106 in the context of a percutaneous medical procedure. In this application the term load is a generic term for force and torque. In one embodiment load sensing system 101 measures axial force acting on EMD 104 as described herein referring to FIGS. 2-5. In one embodiment load sensing system 101 measures torque acting upon EMD 104 about its longitudinal axis as described herein referring to FIG. 6A. In one embodiment load sensing system 101 measures both axial force and torque acting concurrently on EMD 104 referring to FIGS. 6B and 7. In one embodiment axial force measured is $F_{ACTUAL}$ as described herein and torque measured is $T_{ACTUAL}$ as described herein. In one embodiment when the EMD is being inserted the EMD is under compression along the longitudinal axis of the EMD and when the EMD is being withdrawn the EMD is under tension along the longitudinal axis of the EMD.

To sense force and torque acting on a mechanical component having an elongated cylindrical device, a sensor is placed in-line with the elongated cylindrical device or a strain gauge is attached on the elongated cylindrical rod. In interventional catheter and guide wire systems where the elongated cylindrical device is an EMD it may be desirable to measure forces and/or torques acting on the EMD outside of the patient where the sensor is not in line with or attached to the EMD. Measuring forces and torques on an EMD outside of the patient removes the requirement for placing the sensor and related electronics (e.g. cables) inside the blood vessels. While placement of a force and/or torque sensor inside the blood vessels is possible, such as for larger diameter EMDs (e.g. some EP (electrophysiology) catheters with >2 mm diameter), it may be desirable for smaller diameter EMDs with diameters between 0.1 mm and 2 mm to not provide sensors that would be required to be placed within the blood vessels. In manual procedures, the physician relies on his/her fingers to estimate force, however, for the low range of forces and torques that EMDs carry it is very difficult for the physicians to estimate the loads accurately given the small diameter of the devices. In a robotic system, the force and torque acting on the EMDs can be measured using force and torque sensors inside the robotic drive mechanism. However, by placing the sensors inside the drive mechanism, some frictional and inertia parasitic forces and torques are present which prohibit accurate measurement of forces and torques on the EMD. As described below in one embodiment force and/or torque acting on the EMD are measured on a portion of the EMD just before the portion of the EMD enters the next catheter, y-connector or hemostasis valve. The load sensing system can be used for robotic procedures as well as manual procedures performed directly by a physician. For a robotic procedure, the force and/or torque being measured is independent of the drive mechanism in a robotic system and provides accurate measurements of the force and/or torque without mixing parasitic forces and/or torques, added in the drive mechanism, with the actual force/torque being measured.

Figure 1B:
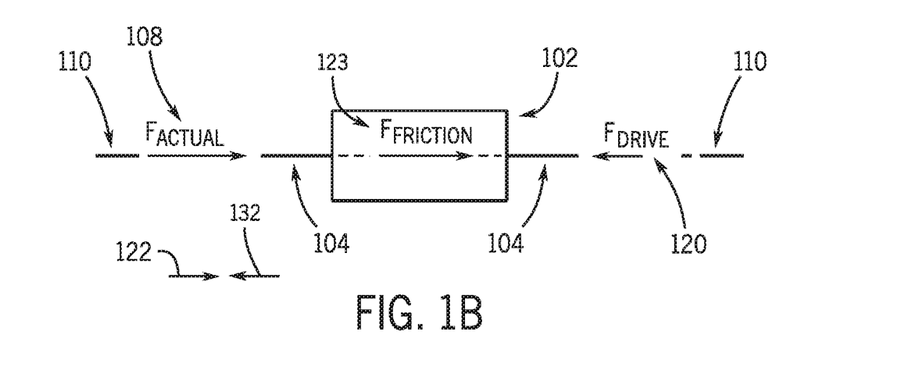
FIG. 1B is a block diagram showing forces acting on an EMD driven through a load sensing system.
Figure 6A:
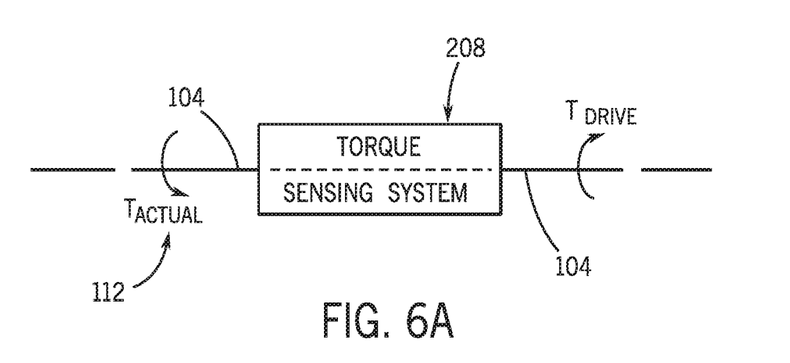
FIG. 6A is a block diagram of a torque sensing system.
Figure 6B:
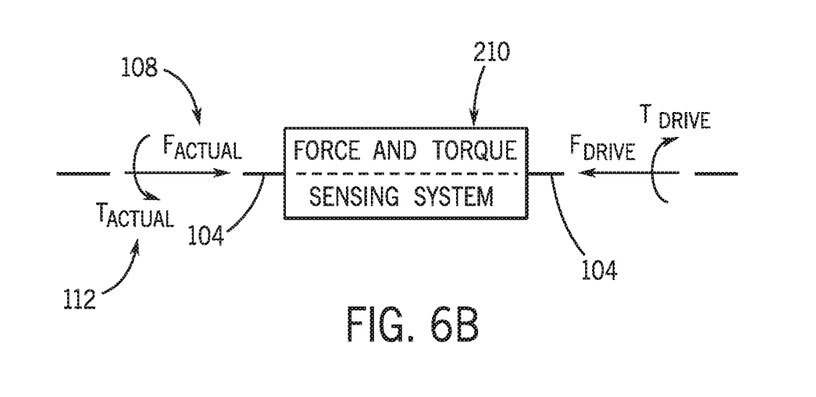
FIG. 6B is a block diagram of a force and torque sensing system.

Referring to FIG. 1A and FIG. 1B a load sensing system 101 detects a load acting EMD 104. Referring to FIG. 1B load sensing system 101 includes a force sensing system 102 that measures an actual axial force 108 described herein as $F_{ACTUAL}$ along a longitudinal axis 110 of the EMD 104 on the proximal side of the y-connector 128 and/or hemostasis valve and distal side of the load sensing system. Referring to FIG. 6A load sensing system 101 includes a torque sensing system 208 that measures a torque 112 described herein as $T_{ACTUAL}$ about the longitudinal axis of the EMD on the proximal side of the load sensing system. Referring to FIG. 6B load sensing system 101 includes a force and torque sensing system 210 that measures both force 108 and torque 112. Referring to FIG. 1B, longitudinal axis 110 is the path extending along a radial center of EMD 104 from a proximal end 116 to a distal end 118 of EMD 104. As disclosed herein in one embodiment EMD 104 moves through drive system 100 in a non-linear path. In one embodiment the non-linear path includes arcuate portions such as a curved portion. In one embodiment the non-linear path includes both arcuate portions and linear or straight portions. In one embodiment the non-linear path is defined as a curvilinear path. In one embodiment the non-linear path is non-straight.

Forces acting on EMD 104 include an axial drive force 120 also referred to herein as $F_{DRIVE}$ applied by drive 106. In one embodiment drive 106 is a robotic drive system that inserts, withdraws, and rotates EMD 104. In one embodiment drive 106 is a person manipulating such as pushing or inserting EMD 104 from the proximal end toward the distal end and/or pulling or withdrawing the EMD from the distal end toward the proximal end, and rotating clockwise or counter clockwise the EMD about the longitudinal axis 110 of the EMD.

Referring to FIG. 1A and FIG. 1B actual axial force 108 is the force on EMD 104 from the direction 122 along the longitudinal axis 110 acting upon the distal portion 124 of force sensing system 102. Note that the term actual axial force is also referred to as axial actual force and translational actual force herein. Actual axial force 108 is the measured force between the proximal end 130 of the y-connector 128 and/or hemostasis valve integrally formed therewith and the distal portion 124 of load sensing system 101. Note that the axial force acting upon a distal portion within a patient (not shown) of the EMD is different than the axial actual force 108 due to additional forces acting upon the EMD between the proximal end 130 of the y-connector 128 and/or hemostasis valve integrally formed therewith and the distal portion of the EMD. The distal portion of the EMD includes the distal tip of the EMD. The actual axial force 108 is comparable with what a physician feels from the EMD with his/her hands in a manual procedure. In one embodiment a proximal end of catheter 105 is operatively connected to a distal end of y-connector 128. EMD 104 extends through a proximal end 130 of y-connector 128 into a lumen of catheter 105. In one embodiment EMD 104 is a guidewire. In one embodiment EMD 104 is another catheter device.

The forces that act upon the EMD between the distal portion 124 of the load sensing system 101 and the distal portion of the EMD include but are not limited to the frictional forces including resistive forces in the load sensing system; y-connector/hemostasis valve guide catheter lumen frictional forces; and vasculature forces.

Friction force $F_{FRICTION}$ 123 is defined as the summation of all frictional forces working against or resisting the insertion of the EMD 104 that act axially, or tangent, to the EMD. Frictional forces such as drag always act opposite to the direction of motion. Frictional force 123 described herein acts in direction 122 when EMD 104 is being inserted in direction 132 opposite direction 122. Referring to FIG. 1B $F_{ACTUAL}$, $F_{DRIVE}$ and $F_{FRICTION}$ include an arrow illustrating the direction in which the respective forces act. In one embodiment $F_{FRICTION}$ 123 is the friction attributable to the friction force in the load sensing system 101. In one embodiment $F_{FRICTION}$ 123 includes the frictional force in the load sensing system 101 as well as frictional forces in the Y-connector 128.

In one embodiment the load sensing system 101 measures the translational actual force along the longitudinal axis for advancing/retracting the EMD 104. In one embodiment the load sensing system 102 measures the torque about the longitudinal axis 110 for rotating the EMD 104. In one embodiment the load sensing system 101 measures both the axial actual force and torque simultaneously.

Figure 2A:
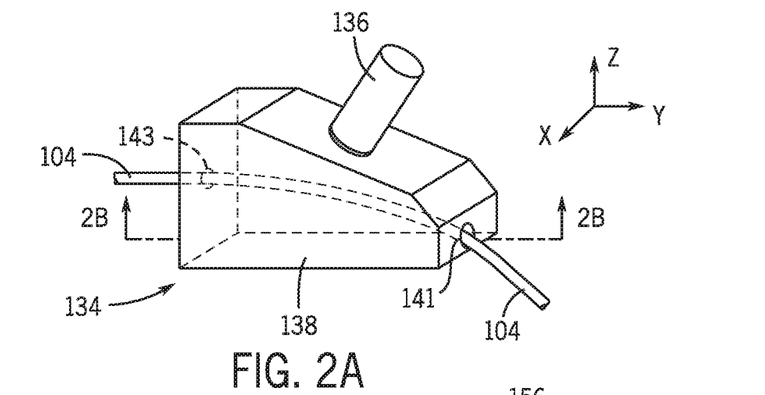
FIG. 2A is an isometric view of a force sensing system.
Figure 2B:
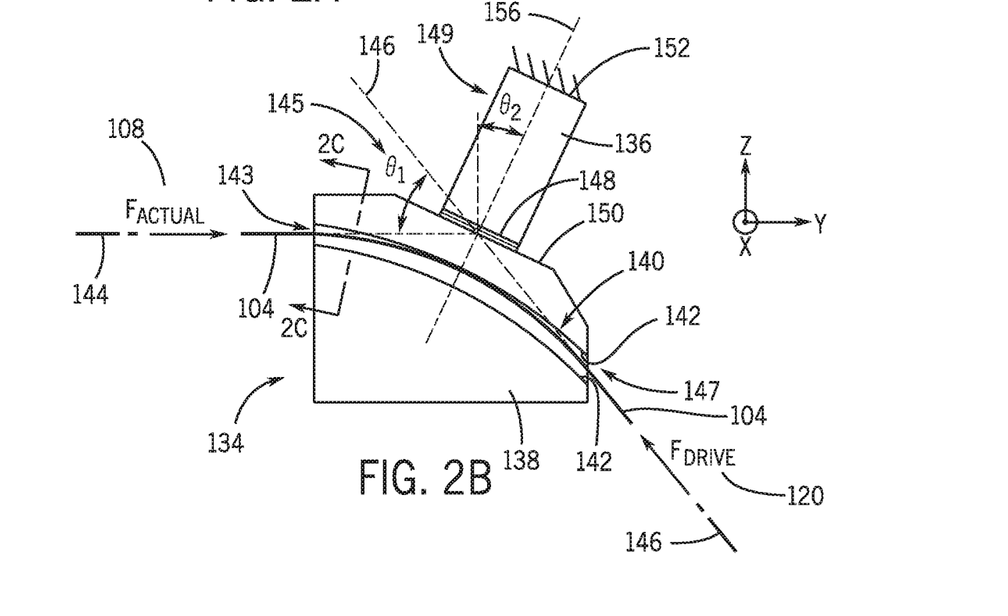
FIG. 2B is a partial cross-sectional view of the force sensing system taken generally along lines 2B-2B of FIG. 2A.
Figure 2C:
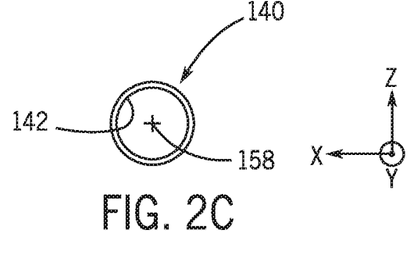
FIG. 2C is a cross-sectional view of a channel of the force sensing system of FIG. 2B taken generally along lines 2C-2C.

Referring to FIG. 2A and FIG. 2B in one embodiment load sensing system includes a support structure 134 secured to a force sensor 136 detecting actual axial force $F_{ACTUAL}$ 108 on the EMD 104 along the EMD axis 110. In one embodiment the longitudinal axis 144 of the actual axial force is colinear with the EMD axis 110. In one embodiment support structure 134 includes a housing 138 with a curved hollowed channel 140, which is a lumen with internal walls 142 serving as a path through which the EMD 104 can pass and be guided. Channel 140 includes a channel opening 141 proximate proximal portion 126 and a channel exit 143 proximate distal portion 124. In one embodiment channel 140 has a wall thickness different from the support structure 134. In one embodiment channel 140 is a tube positioned within a channel defined by support structure 134. Referring to FIG. 2C in one embodiment channel 140 is defined by an aperture extending through support structure 134 in which case internal walls 142 of channel 140 does not have a wall thickness independent of support structure 134.

Local longitudinal axis 144 of actual force 108 immediately adjacent distal portion 124 of force sensing system 102 and local longitudinal axis 146 of drive force 120 immediately adjacent proximal portion 126 of force sensing system are not colinear and are angularly offset by an orientation angle $\theta_1$ 145. In one embodiment angle 145 is fixed and predetermined. The channel entry 147 (proximal end of channel) and channel exit 143 (distal end of channel) are sufficiently narrow that angular changes of EMD entry path local longitudinal axis 146 and exit path local longitudinal axis 144 and angle $\theta_1$ 145 are negligible. In one embodiment, channel entry 147 and channel exit 143 are narrower than the rest of the channel 140. In one embodiment, the clearance between the EMD 104 and the entry channel 147 and exit channel 143 in the y-z plane is small enough and the length of the narrow channel is long enough that the angle of entry axis and exit axis of EMD 104 are known with less than 1° error. In one embodiment angle 145 varies and can be determined by a sensor and be used to calculate $F_{ACTUAL}$. In one embodiment the features described in this paragraph are applicable to the other embodiments disclosed herein.

Force sensor 136 is a transducer that converts compressive or tensile forces into a measurable electrical output (voltage or current). Example transducers include strain-gage-based load cells or load cells that operate by hydraulic, pneumatic, piezoelectric, capacitive, or other means. In one embodiment load cells have fine wires that connect to circuits that either directly or wirelessly transfer information to a processor for signal conditioning and/or computation and processing for display and/or use by a control system for drive system control.

In one embodiment sensor 136 is a contact force sensor. Contact forces are forces acting between two contacting surfaces. Non-contact forces are forces that do not require any physical connection between the two objects involved, such as gravitational force, magnetic force and/or electric forces. These non-contact forces act at a distance. In one embodiment sensor 136 includes a direct contact force sensor. In one embodiment the force sensor includes a non-contact force sensor.

In one embodiment sensor 136 is a single-axis force sensor that measures compressive or tensile force along a single force sensor axis 156. Force sensor axis 156 is angularly offset by orientation angle $\theta_2$ 149. In one embodiment sensor 136 is a two-axis force sensor that measures compressive or tensile forces along a force sensor axis 156 and forces, referred to as shear forces, along an axis perpendicular to the force sensor axis 156. In one embodiment sensor 136 is a three-axis force sensor that measures compressive or tensile forces along a force sensor axis 156 and forces, referred to as shear forces, along two axes perpendicular to the force sensor axis 156.

Referring to FIG. 2B a contact side 148 of force sensor 136 is operatively secured to a first surface 150 of housing 138 by being mechanically connected or fastened such that the two are permanently or semi-permanently attached to one another. Methods for permanent attachment include glue, welds, rivets, seams, press-fits, snap-fits, etc. or any methods in which the two are made integral, such as molded together. Methods for semi-permanent attachment include using discrete hardware components such as screws, bolts, or other threaded fasteners, pins, retaining rings, or any means that afford disassembly.

A second side 152 of force sensor 136 is fixed (grounded). Depending on the elasticity of the force gauge or any components used between the sensor and the support structure, the support structure can have a finite displacement. Assuming the force sensor is stiff, the housing 138 does not move macroscopically. In one embodiment force sensor 136 includes a strain gauge that measures the reaction force on the support structure while deflected less than or equal to 0.001 inch (0.025 mm). In one embodiment force sensor 136 includes a strain gauge that measures the reaction force on the support structure while deflected greater than 0.001 inch (0.025 mm).

Referring to FIG. 2B, $F_{ACTUAL}$ 108 and $F_{DRIVE}$ acting 120 on EMD 104 imparts a resultant force to channel 140 that imparts a reaction force $F_{SENSED}$ 155 to force sensor 136 along its axis 156. In one embodiment in which sensor 136 is a single-axis force sensor, reaction force $F_{SENSED}$ 155 is the measured force from the sensor along its axis 156. In one embodiment in which sensor 136 is a two-axis or three-axis force sensor, reaction force $F_{SENSED}$ 155 is the component of the measured force from the sensor along its axis 156. Reaction force $F_{SENSED}$ 155 from sensor 136 provides a signal to a controller or processor that is used to determine $F_{ACTUAL}$ 108 acting on EMD 104. Assuming friction force $F_{FRICTION}$ 123 is negligibly small, actual axial force $F_{ACTUAL}$ 108 on the EMD 104 is equal to drive force $F_{DRIVE}$ 120. In other words, if $F_{FRICTION}$ 123 is absent, $F_{ACTUAL}=F_{DRIVE}$. In this case with known orientation angles $\theta_1$ 145 and $\theta_2$ 149, $F_{ACTUAL}$ can be determined from the measured reaction force $F_{SENSED}$ 155. Solving force static equilibrium equations gives the equation $F_{ACTUAL}=(F_{SENSED})/[\sin(\theta_2)+\sin(\theta_1-\theta_2)]$. In one embodiment where $F_{FRICTION}$ is negligible there is a direct proportional relationship between the force measured by force sensor 136 and the actual force 108 on EMD 104. Assuming friction force $F_{FRICTION}$ 123 is not negligible, actual axial force $F_{ACTUAL}$ 108 on the EMD 104 is equal to the difference between drive force $F_{DRIVE}$ 120 and friction force $F_{FRICTION}$ 123. In other words, if $F_{FRICTION}$ 123 is present, $F_{ACTUAL}=F_{DRIVE} \, F_{FRICTION}$. In this case with known orientation angles $\theta_1$ 145 and $\theta_2$ 149, $F_{ACTUAL}$ can be determined from the measured reaction force $F_{SENSED}$ 155. Solving force static equilibrium equations gives the equation $F_{ACTUAL}=[F_{SENSED} \, F_{FRICTION} \sin(\theta_1-\theta_2)]/[\sin(\theta_2)+\sin(\theta_1-\theta_2)]$.

It is noted that if orientation angle $\theta_1$ 145 is chosen to be equal to orientation angle $\theta_2$ 149, that is, $\theta_1=\theta_2$, meaning force sensor axis 156 is perpendicular to local longitudinal drive force axis 144, the equation for the actual axial force simplifies to $F_{ACTUAL}=F_{SENSED}/\sin(\theta_2)$, in which case, $F_{ACTUAL}$ can be obtained independent of friction force, $F_{FRICTION}$, in the load-sensing system.

It is noted that if frictional forces between the internal wall 142 of channel 140 and the external surface of EMD 104 are not negligibly small they can be fully characterized. This can be accomplished by a calibration method in which the EMD 104 is advanced slightly and then retracted back to get a baseline value of the frictional forces which can be taken into account when calculating the actual force from the sensor measurements.

Figure 2D:
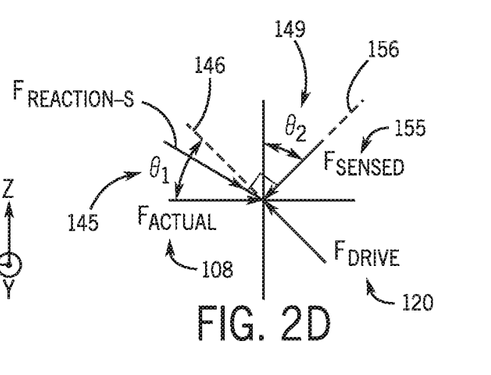
FIG. 2D is a free-body diagram representing the action of forces.

Referring to FIG. 2D, a free-body diagram representing equilibrium of all external forces acting on the force sensing system 102 illustrated in FIGS. 2A-2C is shown. Those forces are actual axial force $F_{ACTUAL}$ 108, drive force $F_{DRIVE}$ 120, and reaction force $F_{REACTION}$ applied by the sensor consisting of the reaction force in the sensor axis direction, $F_{SENSED}$ 155, and the shear reaction force (illustrated as $F_{REACTION-S}$ in FIG. 2D) perpendicular to the sensor axis 156.

Figure 3:
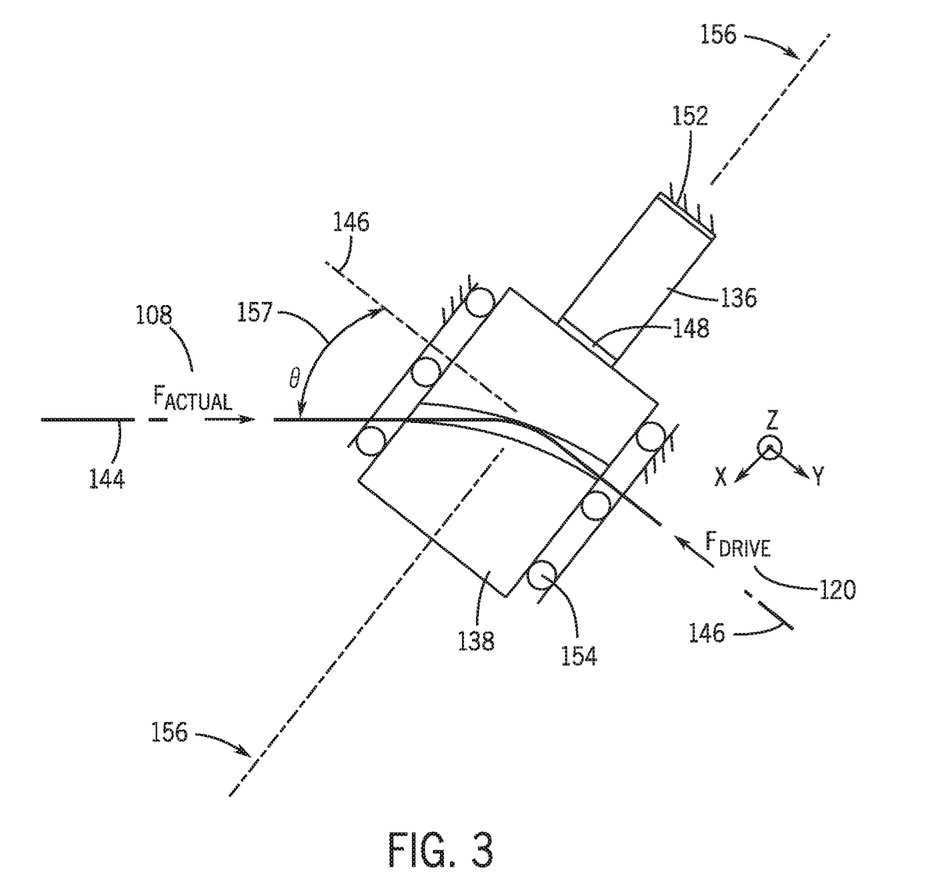
FIG. 3 is a cross-sectional view of a force sensing system including a support structure movably constrained by a linear bearing and a force sensor detecting actual force on the EMD along the EMD axis.

Referring to FIG. 3 in one embodiment axis 144 of the actual force 108 and axis 146 of the drive force 120 are not colinear and are angularly offset by orientation angle $\theta$ 157.

In one embodiment force sensing system 102 housing 138 is secured to a force sensor 136 at sensor contact side 148 with at least one axis of force measurement 156 (X-axis) perpendicular to the local longitudinal drive force axis 146 (Y-axis) to detect actual force 108 on the EMD 104 along the longitudinal axis 144 regardless of the friction force on the EMD along the curved path. In one embodiment, the housing 138 can be supported by a linear motion bearing or linear slide 154 that constrains the housing 138 from applying shear loads to the sensor in any direction other than the measurement direction 156 (that is, it supports the support structure in Y- and Z-directions). The linear motion bearing or linear slide 154 creates low friction or substantially friction-free interface with the support structure so that the forces applied by the bearing/slide to the support structure in the direction of sensor's measurement axis 156 (X-axis) are negligible. In one embodiment low friction force is less than 10% of the actual force. In one embodiment low friction force is less than 5% of the actual force. In one embodiment low friction force is less than 1% of the actual force. In one embodiment, the sensor can support the support structure 138 without use of any linear motion bearing or linear slide 154 while measuring the axial force along the first measurement axis 156 (X-axis). In one embodiment, the sensor can have multiple axes to measure force in one or two additional directions (in addition to X-axis, e.g., Y- and Z-axes) in order to find other forces including but not limiting to the drive force and the friction force in the curved path.

Linear slide 154 may have different types of rolling elements, such as linear ball bearings and linear roller bearings. Other types of linear motion bearings known in the art are contemplated.

Referring to FIG. 3 in one embodiment there is a direct proportional relationship between the force measured by force sensor 136 and the actual force 108 on the EMD 104; i.e., the signal of force sensor 136 is proportional to the actual force after removing offset zero. In this embodiment the mathematical relationship between the actual force $F_{ACTUAL}$ 108 and the force measured from force sensor 136 is derived from force equilibrium to be $F_{SENSED}=(F_{ACTUAL})(\sin \theta)$. This relation is derived by writing a static equilibrium equation in the X direction. Assuming that the friction force caused by the linear bearing in X-direction is negligible, the only other forces in X-direction are the force applied by the sensor 136 to housing 138 (i.e. $F_{SENSOR}$) and X-component of $F_{ACTUAL}$ which is $(F_{ACTUAL})(\sin \theta)$. Based on the static equilibrium equation of housing 138, $F_{SENSED}$ and $(F_{ACTUAL})(\sin \theta)$ should be equal and in opposite directions. Therefore, $F_{SENSED}=(F_{ACTUAL})(\sin \theta)$. The relations defined herein are examples of an algorithm that may be used via a processor to determine the actual forces applied to EMD 104.

Referring to FIG. 2B and FIG. 2C in one embodiment a center 158 of channel 140 lies in a path plane illustrated as the y-z plane in FIG. 2A. However, it is contemplated that channel 140 may have either a circular cross section or a non-circular cross section. Force sensor axis 156 lies in the path plane. Referring to FIG. 3 in one embodiment the measurement axis 156 of force sensor lies in the path plane and is perpendicular to $F_{DRIVE}$ longitudinal axis 146. In one embodiment channel 140 lies in more than one plane. In this embodiment force sensor 136 that can measure multiple components of the force would be employed.

Figure 4A:
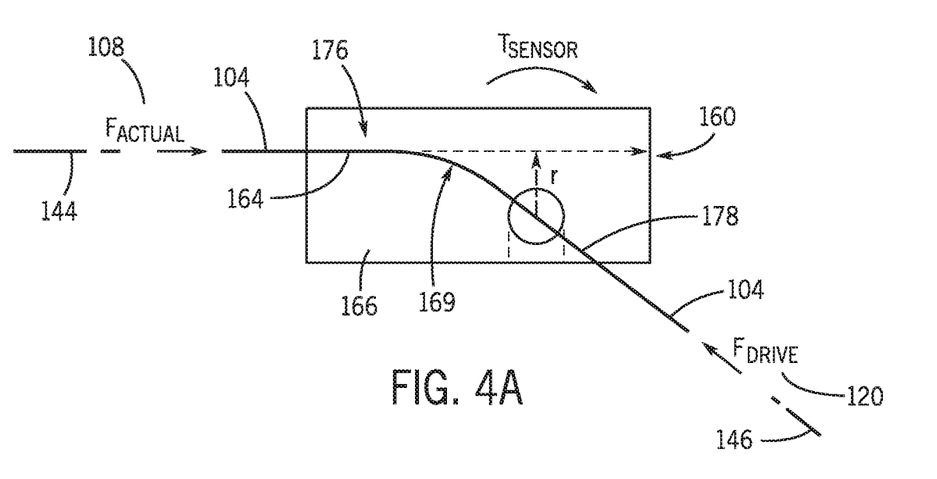
FIG. 4A is a top view of a force sensing system including a support structure that is operatively secured to a torque sensor detecting actual force along the EMD axis.
Figure 4B:
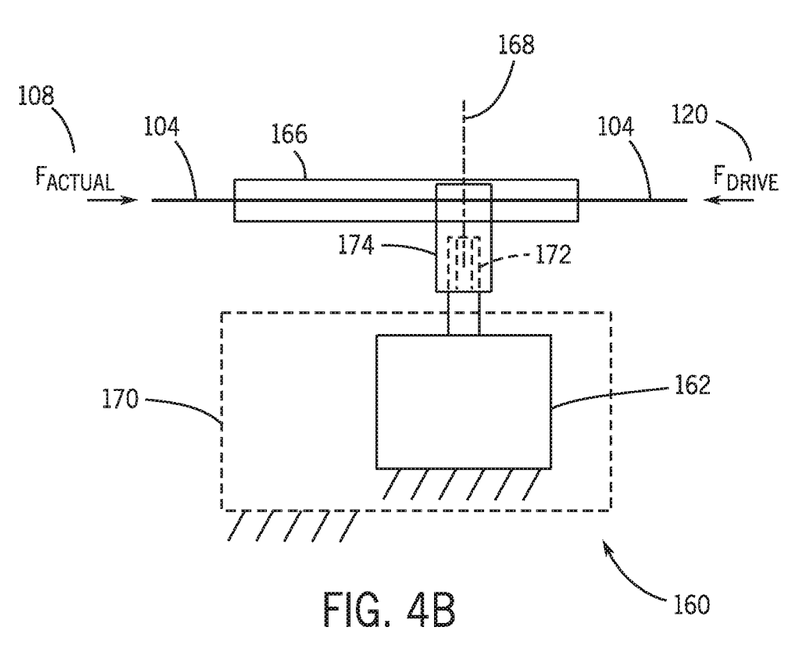
FIG. 4B is a side view of a force sensing system of FIG. 4A.

Referring to FIG. 4A and FIG. 4B a load sensing system 160 measures $F_{ACTUAL}$ 108 using the reaction torque measurements made by a torque sensor 162 as EMD 104 travels through a channel 164 in a path block (also referred to herein as structure or support structure 166. Torque sensor 162 measures the torque about a torque sensor longitudinal axis 168. Torque sensor 162 measures a reaction torque of path block 166 about longitudinal axis 168 of torque sensor 162. Reaction torque is a function of $F_{ACTUAL}$ 108 offset by a distance r from longitudinal axis 168. Channel 164 includes a single radius of curvature 169 within path block 166. The entry path intersects the torque sensor axis.

This embodiment permits the torque sensor to be positioned within a reusable housing 170 referred to as a cassette. Torque sensor 162 can be connected to path block 166 by a simple capstan 172 or a shaft with a key. A sterile barrier (not shown) is removably placed between reusable housing 170 and path block 166 maintaining a sterile environment between path block 166 and housing 170. In one embodiment a sterile barrier can be placed between torque sensor 162 and path block 166 to separate electronics from the disposable or one-use portions that include the path block 166 that is in direct contact with the EMD 104. In one embodiment an O-ring provides a seal between the capstan 172 connected to the torque sensor 162. The capstan 172 is attached to a disposable receiver 174 which in turn is attached to the path block 166 via another seal.

In one embodiment low-friction standard roller/ball bearings can be used, pull and push force both can be captured, and standard sealing can be used.

Referring to FIG. 4A and FIG. 4B path block 166 has an arcuate channel 164 path and is operatively connected to torque sensor 162 via a capstan 172 and capstan receiver 174. Torque sensor 162 measures a reaction torque caused by the $F_{ACTUAL}$ 108 from the EMD 104 on the path block 166 to obtain the force $F_{ACTUAL}$ 108 which can be either a tension force or compression force in the EMD. Force $F_{ACTUAL}=T_{SENSOR}/r$, where $T_{SENSOR}$ is the torque measured by torque sensor 162 and r is the normal distance between the longitudinal axis 168 of sensor 162 to the local longitudinal axis 144 of EMD 104 adjacent distal end of path block. The path block 166 is attached to torque sensor 162 which is grounded via housing 170.

Figure 5A:
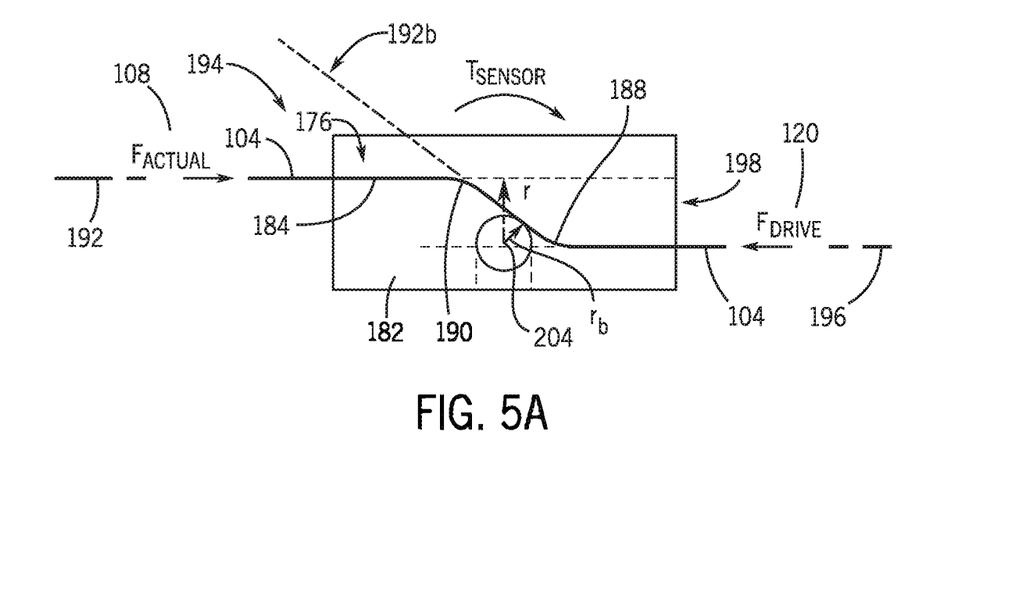
FIG. 5A is a top view of a force sensing system including a support structure with parallel entry and exit paths.
Figure 5B:
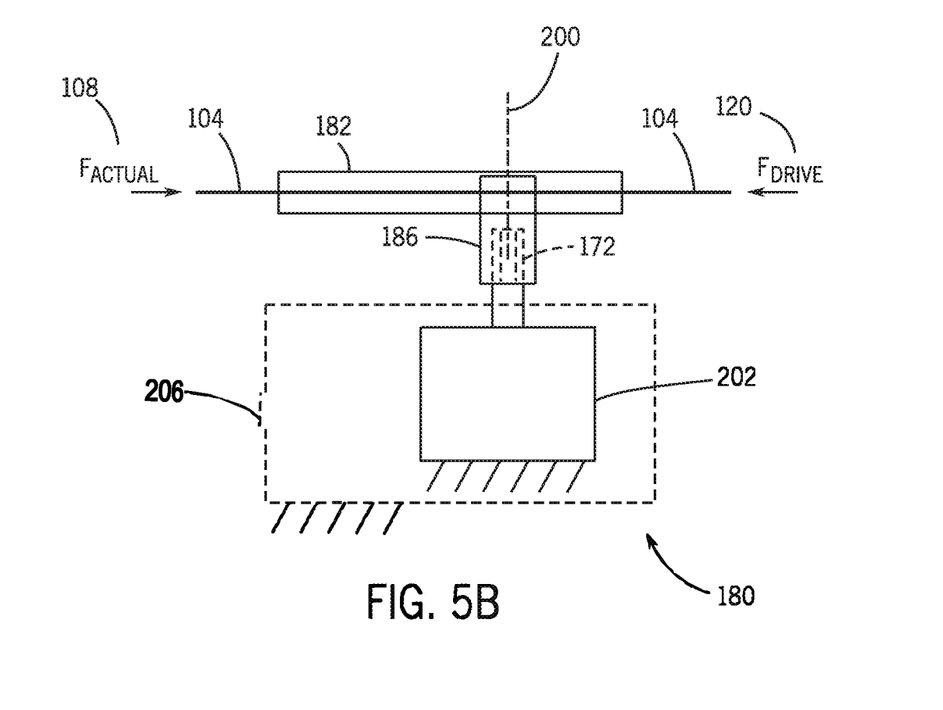
FIG. 5B is a side view of the force sensing system of FIG. 5A.

Referring to FIG. 5A and FIG. 5B load sensing system 180 has a path block 182 with a channel 184 and a capstan receiver 186. In one embodiment it is believed that channel 184 includes a curved path that has at least one inflection point to increase the reaction torque on the torque sensor 204 while the angular difference between the entry path 196 and exit path 192 is reduced. This allows angles as low as zero degree between the local longitudinal axis 192 of the EMD proximate the distal portion 194 of the path block 182 and the local longitudinal axis 196 of the EMD proximate the proximal portion 198 of the path block 182. This can also lead to greater r 198 allowing for a higher reaction torque signal to be sensed by a torque sensor 202 for a given force in the EMD and for a given overall dimension of a support structure. Referring to FIG. 5A, the curved path has one inflection point which allows the local longitudinal axis 192 of the EMD 104 to be parallel to the local longitudinal axis 196 of the EMD 104.

Referring to FIG. 5A the exit path of EMD 104 with no inflection point would be axis 192b for which the offset (normal distance) between the axis of the torque sensor 204 and the axis of the exit path 192 without an inflection point would be small $r_b$. By introducing an inflection point the angle of the exit path can be changed so that the normal distance between exit path 192 and the local longitudinal axis 196 of the EMD increases for the same dimensions of support 198.

Referring to FIG. 5A load sensing system 180, in one embodiment, the angle between the entry path 196 and exit path 192 can be 0 degree; i.e., the load sensing system does not change the direction of the EMD path and only creates an offset r. In general, the angle between the entry path 196 and exit path 192 can be any arbitrary angle depending on user requirements. To achieve the desired angle between the entry path 196 and exit path 192, the channel path can have zero (like FIG. 4a) or one (like FIG. 5A) or more inflection points. Also, the radius of curvature can be constant or varying in a section of the channel 184 or the entire channel 184. Referring to FIG. 5A the local longitudinal axis 196 of EMD 104 is parallel to the local longitudinal axis 192 of EMD 104. To achieve the highest torque signal, local longitudinal axis 196 and local longitudinal axis 192 can lie in the same plane which is normal to the torque sensor axis 200. Referring to FIG. 5A, in one embodiment, the entry path 196 intersects with the axis 200 of the torque sensor so that the measured torque is only a function of $F_{ACTUAL}$ and independent of the friction force between the EMD 104 and the channel 184. In one embodiment, the axis 200 of the torque sensor 202 can be placed so that it intersects the exit line path 192 so that $F_{DRIVE}$ can be found from the measured torque using a similar method that was explained above. In other embodiments, the torque sensor axis 200 can be placed in other positions; however, finding $F_{DRIVE}$ and $F_{ACTUAL}$ would require determination of the friction force caused by the channel 184 on the EMD 104.

In one embodiment the radius of curvature along the path is constant. In one embodiment the radius of curvature along the path varies. In one embodiment the radius of curvature along the path is constant for a first portion and varies for a second portion. In one embodiment there is a first radius of curvature 188 and a second radius of curvature 190. In one embodiment local longitudinal axis 192, local longitudinal axis 196, and the center of channel 184 lie in the same plane. In one embodiment local longitudinal axis 192, local longitudinal axis 196, and the center of channel 184 do not lie in the same plane. When an operator moves EMD 104 from the proximal portion toward the distal portion, portions of EMD 104 enters a channel opening on the proximal portion and exists a channel exit on the distal portion.

Capstan receiver 186 fixedly secured to path block 182 such that a longitudinal axis 200 of the capstan receiver and torque sensor 202 intersects the second local longitudinal axis 196 at a point 204. In one embodiment first longitudinal axis 192 is spaced from second longitudinal axis 196 a normal (perpendicular) distance r. In one embodiment r is greater than or equal to less than or equal to 1 cm. In one embodiment r is sufficiently large to prevent kinking or plastically deforming the EMD through the path.

Torque sensor 202 is grounded via a housing 204 to the base. In one embodiment the base is fixed to the earth. In one embodiment the base is not fixed to the earth. If the base undergoes acceleration or deceleration, correction for inertia forces caused by the moving masses is used. In one embodiment the base is normally fixed to the earth to simplify the calculation method.

Referring to FIG. 5A the entry path defined by local longitudinal axis 196 of EMD 104 into path block 192 entering proximal portion 198 via channel 184 intersects with the longitudinal axis 200 of the torque sensor 202. Referring to FIGS. 4A and 5A instead of measuring reaction forces directly as in FIG. 2A and FIG. 3, the reaction torque is measured. This provides disposable and capital components that are connected by a simple capstan or other coupler known in the art. The use of low-friction standard roller/ball bearings in the coupler minimizes frictional forces acting on the system. In one embodiment $F_{ACTUAL}$ can be determined from the torque sensor 202 output and knowledge of distance "r" for insertion and withdrawal of EMD 104.

Referring to FIG. 5A $F_{ACTUAL} = T_{SENSOR}/r$, where $T_{SENSOR}$ is the torque measured by torque sensor 162 and r is the normal distance between the longitudinal axis 200 of sensor 202 to the local longitudinal axis 192 of EMD 104 adjacent distal side of path block 182.

Referring to FIG. 1A and FIG. 6A load sensing system 101 includes a torque sensing system 208 detecting torque acting upon an EMD 104 being driven by drive 106 in the context of a percutaneous medical procedure. Torque determined by torque sensing system 208 is $T_{ACTUAL}$ applied to EMD 104 proximate the distal portion 124.

Referring to FIG. 1A and FIG. 6B load sensing system 101 includes a force and torque sensing system 210 detecting axial force and torque acting upon EMD 104 being driven by drive 106. In one embodiment force and torque sensing system 210 detects axial force and torque acting concurrently upon EMD 104. Force and torque determined by force and torque sensing system 210 are respectively $F_{ACTUAL}$ and $T_{ACTUAL}$ and applied to EMD 104 proximate distal portion 124.

Figure 7A:
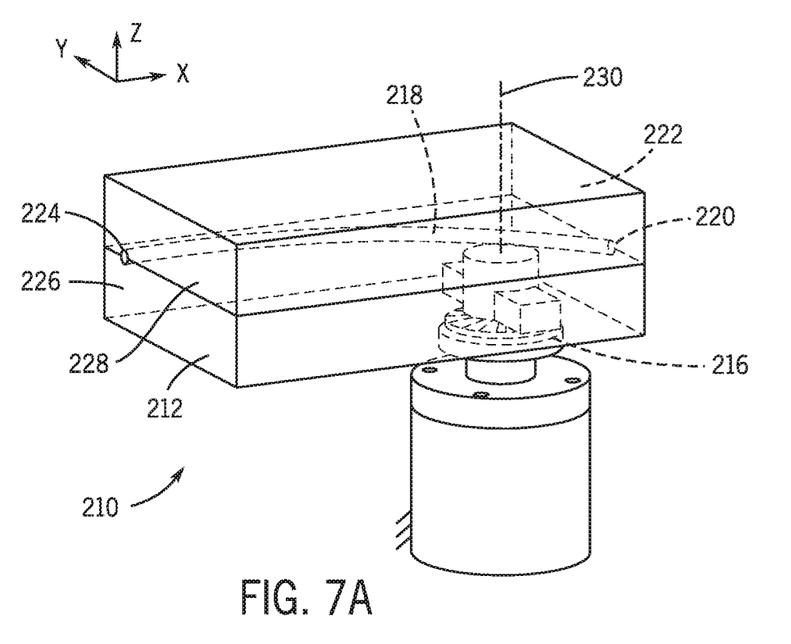
FIG. 7A is an isometric view of a force and torque sensing system.

Referring to FIG. 7A force and torque sensing system 210 includes a path block 212 and a sensor 214 operatively coupled to path block 212 with a coupling system 216. As described below sensor 214 is a multi-axis sensor detecting force and torque applied to path block 212 from EMD 104. In one embodiment multiple single axis sensor are used instead of a single multi-axis sensor 214. In another embodiment, a combination of single axis sensors and multi-axis sensors are used instead of a single multi-axis sensor 214. Path block 212 includes a channel 218 extending therethrough from an opening 220 on proximal side 222 to an exit 224 on distal side 226. In one embodiment channel 218 includes a single radius of curvature. In one embodiment path block 212 includes a channel 218 extending therethrough from an opening 220 on proximal side 222 to an exit 224 on distal side 226. In one embodiment channel 218 includes varying radii of curvature.

In one embodiment channel 218 includes one radius of curvature. In one embodiment channel 218 includes more than one radii of curvature equaling two, three, four or more.

Figure 8A:
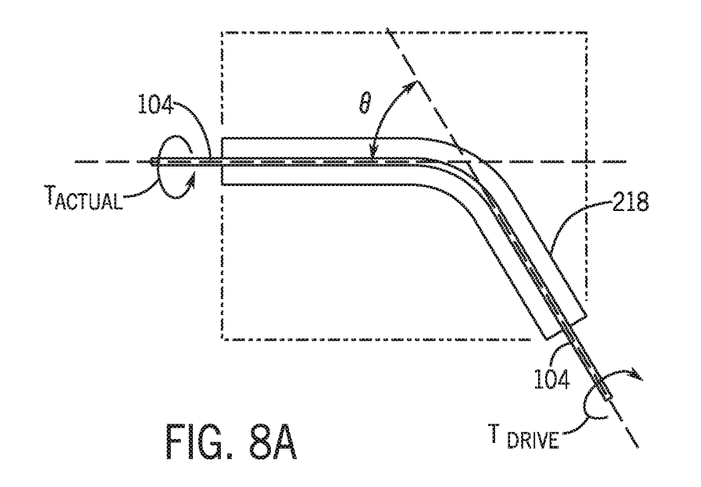
FIG. 8A is a partial cross-sectional view showing the drive torque and actual torque acting on an EMD through a channel.
Figure 8B:
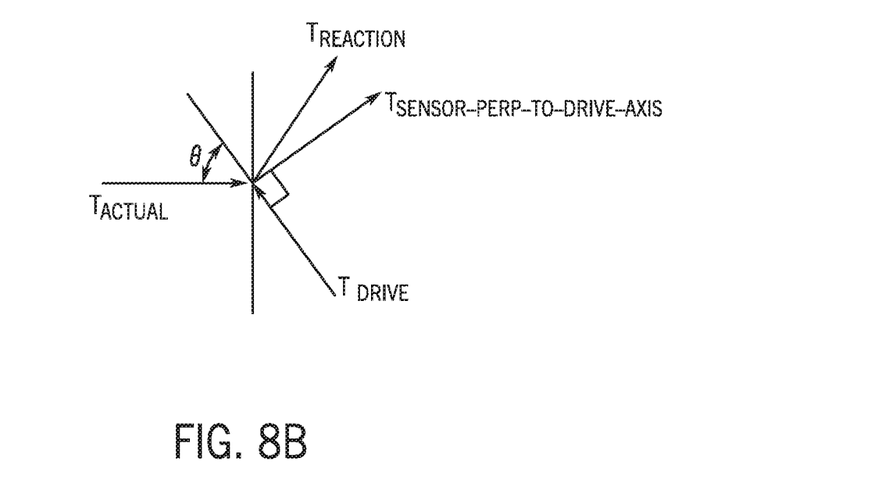
FIG. 8B is a free-body diagram showing torques as vectors on the EMD of FIG. 8A.

Referring to FIG. 7A, FIG. 8A, and FIG. 8B, torque ($T_{ACTUAL}$) acting on EMD 104 within channel 218 and drive torque $T_{DRIVE}$ impart a reaction torque $T_{REACTION}$ on the path block or support structure 212 (FIG. 7A) and a support structure (FIG. 8A) that can be measured by sensor 214 ($T_{SENSOR}$). The torque can be specifically measured about an axis perpendicular to the entry axis of the EMD ($T_{SENSOR-PERP-TO-DRIVE-AXIS}$) to the support structure in order to eliminate the effect of frictional torque and drive torque $T_{DRIVE}$ in determination of actual torque $T_{ACTUAL}$.

Referring to FIG. 8B, where torques are indicated as vectors with arrows, actual torque $T_{ACTUAL}$ can be determined directly from the measured torque from the equation $T_{SENSOR-PERP-TO-DRIVE-AXIS} = (T_{ACTUAL})(\sin \theta)$ where $T_{SENSOR-PERP-TO-DRIVE-AXIS}$ is the component of the reaction torque perpendicular to the drive axis and the reaction torque is the vector sum of the actual torque and drive torque. The reaction torque is sensed by sensor 214 and is equal to the total sensed torque.

Figure 9A:
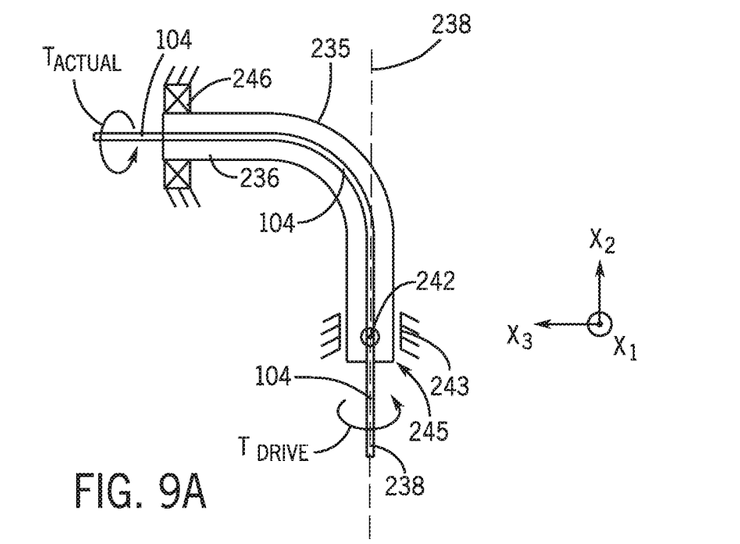
FIG. 9A is a top view of a torque sensing system including a rotational bearing and a force sensor detecting actual torque on the EMD.

Referring to FIG. 9A8A, $T_{ACTUAL}$ can be determined by measuring the reaction force applied by EMD 104 to path block 212 which is detected by force sensor 214. $T_{ACTUAL}$ causes the portion of EMD 104 within channel 218 to rotate out of a path plane 228 thereby imparting a force to path block 212 that is detected by sensor 214. In one embodiment, the support structure can be externally supported by a low friction bearing at the exit port and by a force sensor at the entry port and perpendicular to the plane where the axis of the bearing is aligned with the entry axis. In one embodiment, the axis of the bearing has an angle offset of 90 degree relative to the exit port. In such a case, $T_{ACTUAL}$ can be determined as the product of the force sensed by sensor 214 and the distance between the exit port to the sensor.

Referring to FIG. 7A, in one embodiment $T_{ACTUAL}$ results in a reaction torque vector in XY plane applied to path block 212 and $F_{ACTUAL}$ results in a second reaction torque about longitudinal axis 230 (normal to XY plane) both of which are sensed by the multi-axis sensor 214. Since the two reaction torque vectors are orthogonal, each of them can be measured independently using a multi-axis torque sensor. Also, as mentioned above, $F_{ACTUAL}$ and $T_{ACTUAL}$ can be determined by measuring reaction forces rather than reaction torques. Therefore, a multi-axis force and torque sensor 214 can alternatively be used to determine $F_{ACTUAL}$ and $T_{ACTUAL}$ from the force reactions and/or a combination of force and torque reactions. Since the reaction forces applied by the EMD to the support structure are orthogonal, $F_{ACTUAL}$ and $T_{ACTUAL}$ can be determined independently. Multi-axis sensor 214 provides a signal to a controller or processor that determines the $F_{ACTUAL}$ and $T_{ACTUAL}$ acting on EMD 104.

Force and Torque load sensing system 210 determines $F_{ACTUAL}$ and $T_{ACTUAL}$ through an algorithm. In one embodiment the multi axis sensor 214 provides signals via a wire that can carry electronic signals to a signal conditioner box that includes electronics such as amplifiers and/or signal conditioning circuits that process the signals and forwards one or more values to a display either directly to a monitor or computer monitor via a processor. In one embodiment multi-axis sensor 214 provides multiple values depending on the load being applied along the multi axes being measured. The processor utilizing an algorithm converts the values into a representation of $F_{ACTUAL}$ and $T_{ACTUAL}$. In one embodiment the relative change in values provides information to a user even if the values are not an in metric or US customary units such as Newtons (N) or lbs. The relative increase and/or decrease of the values provides information that a user or processor can interpret to provide an approximation or indication of forces acting upon a distal end of EMD 104.

Referring to FIG. 7A sensor 214 is grounded relative to path block 212. In one embodiment sensor 214 is fixedly secured to a housing which in turn is operatively grounded to the base (normally earth).

Figure 7B:
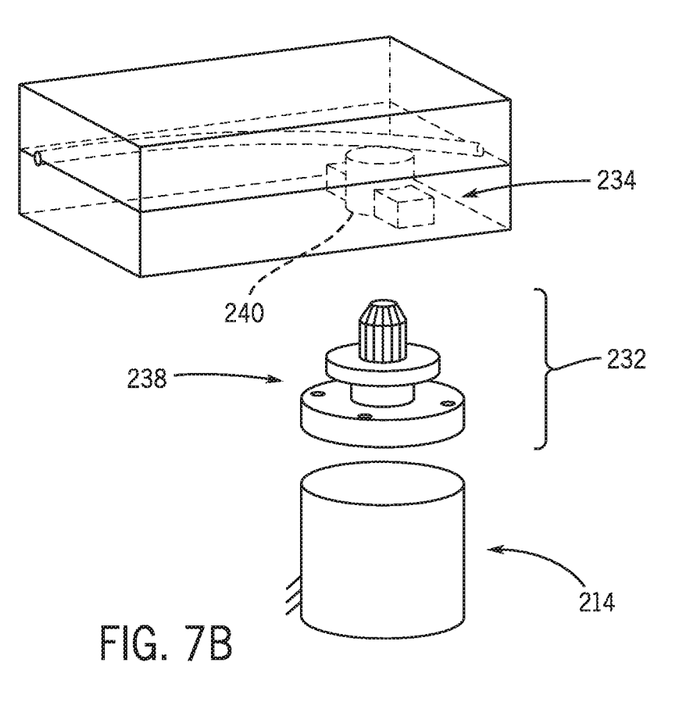
FIG. 7B is an exploded view of the force and torque sensing system of FIG. 7A.

Referring to FIG. 7B a first coupler 232 is secured to sensor 214. A second coupler 234 is secured to path block 212 and is removably coupled to first coupler 232. In one embodiment first coupler 232 includes a capstan that is removably received within a keyed capstan receiver. The capstan is shown only as a simple example of attachment. The attachment can be done through numerous methods such as bolting block 212 to the multi-axis sensor 214.

Referring to FIG. 7A and FIG. 7B, path block 212 can have a slot (not shown) to allow EMD 104 to be radially loaded directly into channel 218 along a radius as opposed to axially loaded in which case a distal end of EMD is inserted into entry opening 220 and threaded through channel 218 until its distal end exits distal opening 224. In one embodiment path block 212 includes a cover that operatively can be moved from a closed orientation covering channel 218 to a loading orientation in which EMD 104 can be radially loaded into channel 218. The cover (not shown) can be pivotally secured to a lower portion of path block 212 or can be removably fastened to lower portion of path block 212. In one embodiment capstan receiver or second coupler is integrally formed with path block 212 such that capstan receiver opening is adjacent a bottom surface of path block 212.

Figure 9B:
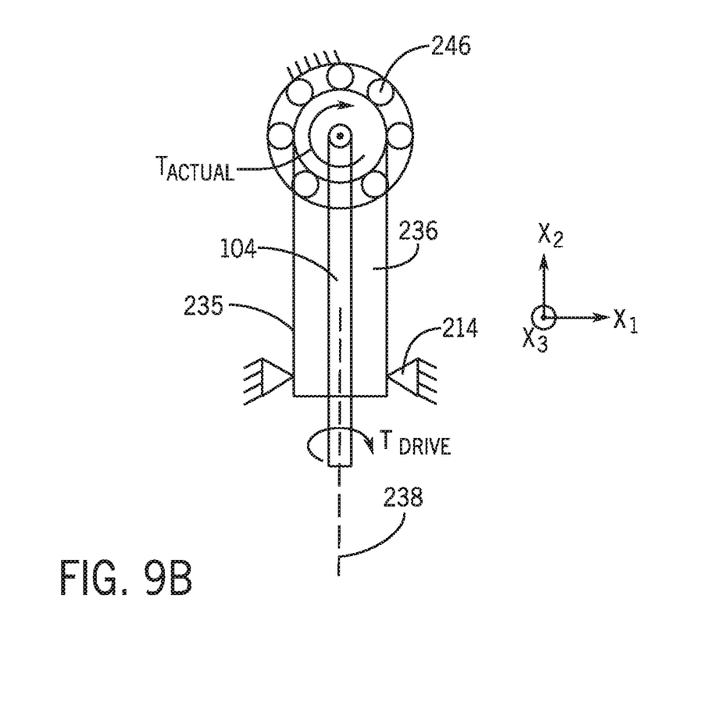
FIG. 9B is a side view of the torque sensing system of FIG. 9A.

Referring to FIG. 9A and FIG. 9B one embodiment of a load sensing system 160 measures $T_{ACTUAL}$ using the reaction force measured by a force sensor 136 or 214 as EMD 104 travels through a flexible arcuate channel 236 defined by a structure 235. At one end of channel 236, where drive torque $T_{DRIVE}$ is applied to EMD 104, the walls of the channel are constrained in the $x_2$-$x_3$ axis plane and is supported by the force sensor 242 in $x_1$ direction, so that force sensor 214 senses the reaction force in $x_1$ direction. At one end of channel 236, where actual torque $T_{ACTUAL}$ is applied to EMD 104, the walls of the channel are constrained in the $x_1$-$x_2$ axis plane by a rotational bearing 246 and the channel would be free to rotate about the $x_3$ axis if sensor 214 was not attached to the channel. Stated another way in one embodiment $T_{ACTUAL}$ acting on EMD 104 imparts a force to channel 236 that imparts a force to force sensor 214 along its axis 242. Force sensor 136 provides a signal to a controller or processor that determines $T_{ACTUAL}$ acting on EMD 104. Referring to FIG. 9A a guide 243 constrains structure 235 proximate proximal end 245 of structure 235. In one embodiment structure 235 has a circular cross-section. Stated another way in one embodiment structure 235 is a tubular member defining a channel 236 extending therethrough.

Rotational bearing 246 may have different types of rolling elements, such as linear ball bearings and linear roller bearings. Other types of rotational motion bearings known in the art are contemplated.

For the embodiments described herein sensors described herein detect $F_{ACTUAL}$ 108 and $T_{ACTUAL}$ 112 by measuring the reaction load on the support structure caused by the force and or torque acting on the EMD that in turn acts upon the channel wall. In one embodiment, for the various load sensing systems described herein, the load (force and/or torque) applied to the channel wall is independent of a magnitude of bending, deflection or buckling of the EMD. In one embodiment structural supports described herein include a slit extending through and along the entire channel wall to permit radial loading of the EMD into the channel between the channel entry and channel exit. In one embodiment radial loading is also referred and is the same as side loading where the side may be from any side of the channel. Radial loading and side loading are different from axial loading in which a terminal end of the EMD must be inserted into the entry of the channel until the terminal end exits the exit of the channel. In one embodiment an exit longitudinal axis of the EMD extends in a direction distally from the exit and is spaced from an entry longitudinal axis of the EMD that extends in a direction proximally from the entry. In one embodiment the entry longitudinal axis and the exit longitudinal axis of the EMD are substantially linear. In one embodiment the entry longitudinal axis and the exit longitudinal axis of the EMD are substantially linear for at least 25 mm (1 in).

In one embodiment the exit side of channel 236 is supported by a bearing and the entry side of channel 236 is supported by force sensor 214 which prevents motion. Stated another way the reaction force applied to force sensor 214 from channel 236 supports it and maintains its position by reacting to the force applied by the EMD to the channel.

The force exerted from the EMD to the curved channel measured by force sensor 214 can be translated/converted into $T_{ACTUAL}$, the torque applied to the EMD. The shape of the curved path can have any general form of curved path with or without inflection point(s). In one embodiment the entry axis and exit axis are linear for at least 25 mm (1 in). In one embodiment the entry axis and exit axis are linear for more than 25 mm (1 in) and in one embodiment the entry axis and the exit axis are linear for the same distance. In one embodiment the entry axis and the exit axis are linear for different distances. The angle between the entry and exit paths should normally be fixed for simplification, but in one embodiment the angle can vary as long as the angle is known or measurable at each moment. In one embodiment the load sensing embodiments described herein sense a force between 0 N and 5 N. In one embodiment the load sensing embodiments described herein sense a force between 0 N and 10 N. In one embodiment the load sensing embodiments described herein sense a force between 0 N and 20 N. Where "N" is an abbreviation for a newton unit of measure for force.

Although the present disclosure has been described with reference to example embodiments, workers skilled in the art will recognize that changes may be made in form and detail without departing from the spirit and scope of the defined subject matter. For example, although different example embodiments may have been described as including one or more features providing one or more benefits, it is contemplated that the described features may be interchanged with one another or alternatively be combined with one another in the described example embodiments or in other alternative embodiments. Because the technology of the present disclosure is relatively complex, not all changes in the technology are foreseeable. The present disclosure described is manifestly intended to be as broad as possible. For example, unless specifically otherwise noted, the definitions reciting a single particular element also encompass a plurality of such particular elements.

What is claimed is:

1. An apparatus comprising:
   a base;
   a support including a non-straight channel extending therethrough, the channel configured to receive an elongated medical device (EMD) extending through the channel;
   a slide disposed between the support and the base, where the support moves along the slide and relative to the base in a single degree of freedom in response to a reaction load on the support caused by a first load acting on the EMD and imparted to a wall of the channel by the EMD; and
   a sensor against which the support is biased due to the movement of the support relative to the base in the single degree of freedom, the sensor configured to measure the reaction load based on the bias.

2. The apparatus of claim 1, further including a processor to determine the first load based on the reaction load.

3. The apparatus of claim 2, wherein the first load applied to the EMD is determined independent of a magnitude of bending, deflection or buckling of the elongated medical device.

4. The apparatus of claim 2, wherein the channel is non-straight and has a friction sufficiently low so that the error caused by the friction force in determination of the load acting on the EMD is below the acceptable error.

5. The apparatus of claim 2, wherein the channel is non-straight and has a finite friction, a load magnitude acting on the EMD at an entry of the channel is higher than a load magnitude acting on the EMD at an exit of the channel, wherein the entry of the channel is closer to a drive mechanism driving the EMD than the exit of the channel; wherein a finite friction between the EMD and the channel is characterized and is corrected for in determination of the load magnitude acting on the EMD at an exit entry of the channel.

6. The apparatus of claim 2, wherein the first load applied to the EMD is determined independent of friction between the EMD and the channel, wherein the channel is non-straight.

7. The apparatus of claim 1, wherein the first load includes a force acting along a longitudinal axis of the elongated medical device in one of a first direction (compression) and a second direction (tension).

8. The apparatus of claim 1, wherein the first load includes a torque acting on the elongated medical device in one of a first direction (CW) and a second direction (CCW) about the longitudinal axis of the elongated medical device.

9. The apparatus of claim 1, wherein the support is fixed relative to the base proximate an entry of the channel and proximate an exit of the channel, wherein an entry axis and an exit axis are non-colinear.

10. The apparatus of claim 9, wherein the entry defines the entry axis and the exit defines the exit axis, the entry axis and exit axis being non-colinear.

11. The apparatus of claim 9, wherein a portion of the EMD enters the channel at the entry and moves through the channel and exits the channel at the exit, wherein the load measured is the load acting on the EMD proximate the exit.

12. The apparatus of claim 1, wherein the sensor is positioned within a reusable base and the support is positioned within a cassette removably coupled to the base.

13. The apparatus of claim 12, wherein the cassette and the reusable base are separated by one or more sterile barriers.

14. The apparatus of claim 1, wherein the sensor is a multi-axis sensor detecting a load along more than one axis.

15. The apparatus of claim 14 wherein the multi-axis sensor is used to determine an actual load axial force and an actual torque applied to the EMD independent of a friction force between the EMD and the channel by measuring a component of a reaction force and a torque imparted to the channel by the EMD perpendicular to the direction of axial drive force vector and a torque drive force vector.

16. The apparatus of claim 1, wherein the first load is an axial force and the sensor is a torque sensor measuring a reaction torque on the support.

17. The apparatus of claim 16 where an axis of an entry of the channel intersects with an axis of the torque sensor so that the reaction torque measured by the sensor is independent of a friction force between the EMD and the channel and is only a function of an actual force acting on the EMD.

18. The apparatus of claim 1, further including a second load, wherein the first load is a force and the second load is a torque and the sensor is a multi-axis sensor measuring reaction force and reaction torque on the support to determine the force and the torque applied to the EMD.

19. A method of measuring a load on an elongated medical device including:
   providing a base and a support including a non-straight channel extending therethrough;
   moving an elongated medical device through the channel to cause the support to move relative to the base along a slide disposed between the support and the base in a single degree of freedom in response to a reaction load applied to the support by the elongated medical device; and measuring the reaction load applied to the support from the elongated medical device using a sensor against which the support is biased due to the movement of the support relative to the base in the single degree of freedom, wherein the reaction load is related to a first load acting on the elongated medical device.

20. An apparatus comprising:

a base;

a support including a non-straight channel extending therethrough, the channel configured to receive an elongated medical device (EMD) extending through the channel;

a slide disposed between the support and the base, where the support moves along the slide and relative to the base in a single degree of freedom in response to a reaction load on the support caused by a first load imparted by the EMD on the wall of the channel; and a sensor against which the support is biased due to the movement of the support relative to the base in the single degree of freedom, the sensor configured to measure the reaction load based on the bias.

* * * * *